(12) United States Patent
Kim et al.

(10) Patent No.: US 10,342,494 B2
(45) Date of Patent: Jul. 9, 2019

(54) TOUCH PANEL APPARATUS FOR SENSING A BIOSIGNAL AND METHOD OF ACQUIRING INFORMATION ABOUT RESPIRATION OF USER USING THE SAME

(71) Applicant: SAMSUNG ELECTRONICS CO., LTD., Suwon-si (KR)

(72) Inventors: Sunkwon Kim, Suwon-si (KR); Jaemin Kang, Seoul (KR); Yongjoo Kwon, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 552 days.

(21) Appl. No.: 15/078,034

(22) Filed: Mar. 23, 2016

(65) Prior Publication Data
US 2017/0055910 A1 Mar. 2, 2017

(30) Foreign Application Priority Data
Aug. 24, 2015 (KR) .................. 10-2015-0118874

(51) Int. Cl.
*A61B 5/00* (2006.01)
*A61B 5/08* (2006.01)
*A61B 5/091* (2006.01)
*A61B 5/113* (2006.01)
*G06F 3/044* (2006.01)

(52) U.S. Cl.
CPC .......... *A61B 5/6898* (2013.01); *A61B 5/0809* (2013.01); *A61B 5/0816* (2013.01); *A61B 5/091* (2013.01); *A61B 5/113* (2013.01); *A61B 5/7203* (2013.01); *A61B 5/725* (2013.01); *A61B 5/7246* (2013.01); *A61B 5/742* (2013.01); *A61B 5/7475* (2013.01); *G06F 3/044* (2013.01)

(58) Field of Classification Search
None
See application file for complete search history.

(56) References Cited

U.S. PATENT DOCUMENTS 4,966,155 A * 10/1990 Jackson ................ A61B 5/222
                                                            600/483
5,086,776 A * 2/1992 Fowler, Jr. ........... A61B 5/0205
                                                            600/452
(Continued)

FOREIGN PATENT DOCUMENTS

EP        3023870 A1    5/2016
JP     2008-241717 A   10/2008
(Continued)

OTHER PUBLICATIONS

Communication dated Jan. 30, 2017, issued by the European Patent Office in European Patent Application No. 16171608.9.

*Primary Examiner* — Patricia Mallari
*Assistant Examiner* — Jairo H Portillo
(74) *Attorney, Agent, or Firm* — Sughrue Mion, PLLC

(57) ABSTRACT

A touch panel apparatus for sensing a biosignal and a method of acquiring information about respiration of a user by the touch panel apparatus are provided. The touch panel apparatus includes a touch panel configured to sense a biosignal of a user based on a touch input through the touch panel; a detector configured to detect a respiratory signal from the biosignal; and a processor configured to acquire information about respiration of the user based on characteristics of the detected respiratory signal.

24 Claims, 13 Drawing Sheets

(56) References Cited

U.S. PATENT DOCUMENTS

| | | | |
|---|---|---|---|
| 6,514,218 B2* | 2/2003 | Yamamoto | A61B 5/103 600/587 |
| 7,641,618 B2 | 1/2010 | Noda et al. | |
| 2004/0077934 A1* | 4/2004 | Massad | A61B 5/0205 600/300 |
| 2005/0054941 A1* | 3/2005 | Ting | A61B 5/0408 600/529 |
| 2005/0215915 A1* | 9/2005 | Noda | A61B 5/1102 600/535 |
| 2006/0060198 A1* | 3/2006 | Aylsworth | A61B 5/0205 128/204.23 |
| 2009/0054792 A1* | 2/2009 | Sato | A61B 5/02444 600/484 |
| 2010/0044069 A1* | 2/2010 | Stewart | B29C 70/882 174/110 SR |
| 2010/0324437 A1* | 12/2010 | Freeman | A61B 5/085 600/529 |
| 2011/0021902 A1* | 1/2011 | Kim | A61B 5/0432 600/391 |
| 2011/0150291 A1 | 6/2011 | Jung | |
| 2014/0206974 A1 | 7/2014 | Volpe et al. | |
| 2014/0276163 A1* | 9/2014 | Thakur | A61B 5/024 600/528 |
| 2015/0032009 A1* | 1/2015 | LeBoeuf | A61B 5/00 600/476 |
| 2015/0201884 A1* | 7/2015 | Ashokan | A61B 5/4872 702/19 |
| 2016/0147367 A1 | 5/2016 | Kim et al. | |

FOREIGN PATENT DOCUMENTS

| | | |
|---|---|---|
| JP | 2013-158593 A | 8/2013 |
| JP | 2014-210127 A | 11/2014 |
| KR | 10-2010-0044384 A | 4/2010 |
| KR | 10-1082210 B1 | 11/2011 |
| KR | 10-2016-0061211 A | 5/2016 |
| WO | 2013/179031 A1 | 12/2013 |

* cited by examiner

TOUCH PANEL APPARATUS FOR SENSING A BIOSIGNAL AND METHOD OF ACQUIRING INFORMATION ABOUT RESPIRATION OF USER USING THE SAME

CROSS-REFERENCE TO RELATED APPLICATION

This application claims priority from Korean Patent Application No. 10-2015-0118874, filed on Aug. 24, 2015 in the Korean Intellectual Property Office, the disclosure of which is incorporated herein by reference in its entirety.

BACKGROUND

1. Field

Apparatuses and methods consistent with exemplary embodiments relate to sensing a biosignal and acquiring information about respiration of a user using a touch panel.

2. Description of the Related Art

A spirometer may be used to acquire information about respiration of a person. A user may measure respiratory signals using a spirometer by breathing in and out while holding a tube connected to the spirometer in his/her mouth or wearing a respiratory mask.

SUMMARY

One or more exemplary embodiments provide a touch panel apparatus that obtains a biosignal from a user using a pair of electrode layers that senses a touch input signal of the user and a method of acquiring information about respiration based on the biosignal.

According to an aspect of an exemplary embodiment, there is provided a touch panel apparatus for sensing a biosignal including: a touch panel configured to sense a biosignal of a user based on a touch of the user input through the touch panel; a detector configured to detect a respiratory signal from the sensed biosignal; and a processor configured to acquire information about respiration of the user based on characteristics of the detected respiratory signal.

The touch panel may include a pair of electrode layers and be configured to sense the biosignal based on capacitance in the electrode layer pair, and the capacitance may change according to the respiration of the user.

The touch panel may include a pair of electrode layers, and the pair of electrode layers may include a first electrode layer partitioned into a plurality of regions corresponding to an actuator and a sensor and a second electrode layer configured to block noise from entering the first electrode layer.

The detector may include a band pass filter configured to pass a signal in a respiratory frequency band among the sensed biosignal and at least one noise removal filter configured to remove noise from the passed signal.

The processor may detect peaks of the respiratory signal, measure a time interval between adjacent peaks among the detected peaks, and determine a respiration rate of the user based on the measured time interval.

The processor may detect peaks of the respiratory signal, measure a slope between a minimum peak and a maximum peak upon an inhalation for each respiratory cycle among the detected peaks, and determine respiratory intensity of the user based on the measured slope.

The processor may detect peaks of the respiratory signal, measure an area of sections that corresponds to an inhalation and an exhalation for each respiratory cycle and is defined by at least three of the detected peaks, and determine a respiratory volume of the user based on the measured area.

The processor may compare respiratory signals before and after exercise of the user to determine an exercise load applied to the user during the exercise or information about a recovery speed at which a respiration rate after the exercise returns to a respiration rate before the exercise.

The touch panel apparatus may further include a feedback unit configured to inversely amplify a respiration-removed signal that is obtained by removing the respiratory signal from the biosignal, and output the inversely amplified respiration-removed signal, in which the touch panel receives the respiration-removed signal as a negative feedback to adjust the biosignal.

The touch panel apparatus may be interoperable with a user terminal and configured to transmit information about the respiratory signal to the user terminal.

According to an aspect of another exemplary embodiment, there is provided a method of acquiring information about respiration of a user by a touch panel apparatus including: sensing a biosignal of the user based on a touch of the user sensed by the touch panel apparatus; detecting a respiratory signal from the sensed biosignal; and acquiring information about respiration of the user based on characteristics of the detected respiratory signal.

The sensing the biosignal may include sensing the biosignal based on capacitance in an electrode layer pair included in the touch panel apparatus, and the capacitance may change according to the respiration of the user.

The sensing the biosignal may include sensing the biosignal using a first electrode layer partitioned into a plurality of regions and configured to operate as an actuator and a sensor and a second electrode layer configured to operate as a shield that blocks noise from entering the first electrode layer.

The detecting the respiratory signal may include passing a signal in a respiratory frequency band among the sensed biosignal; blocking a signal out of the respiratory frequency band among the sensed biosignal; and removing noise from the passed signal.

The acquiring the information may include detecting peaks of the respiratory signal, measuring a time interval between adjacent peaks among the detected peaks, and determining a respiratory rate of the user based on the measured time interval.

The acquiring the information may include detecting peaks of the respiratory signal, measuring a slope between a minimum peak and a maximum peak upon an inhalation for each respiratory cycle among the detected peaks, and determining respiratory intensity of the user based on the measured slope.

The acquiring the information may include detecting peaks of the respiratory signal, measuring an area of sections that corresponds to an inhalation and an exhalation for each respiratory cycle and is defined by at least three of the detected peak, and determining a respiratory volume of the user based on the measured area.

The acquiring the information may include comparing respiratory signals before and after exercise of the user to determine an exercise load applied to the user during the exercise or a recovery speed at which a respiration rate after the exercise returns to a respiration rate before the exercise.

The sensing the biosignal may include receiving a respiration-removed signal, which is obtained by removing a respiratory signal from a biosignal, as a negative feedback to adjust the biosignal.

According to an aspect of still another exemplary embodiment, there is provided a non-transitory computer readable storage medium storing a program that is executable by a computer to perform the above-described method.

According to an aspect of still another exemplary embodiment, there is provided a touch panel apparatus including: a touch panel configured to sense a touch of a user and recognize the touch as a biosignal in response to the touch panel apparatus being in a respiration measurement mode; a detector configured to detect a number of maximum peaks of the biosignal within a predetermined time period; and a processor configured to determine a respiration rate of the user based on the detected number of maximum peaks.

The touch panel apparatus may be configured to store information of an age of the user, and the processor may be further configured to determine a health state of the user based on the determined respiration rate and the information of the age.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
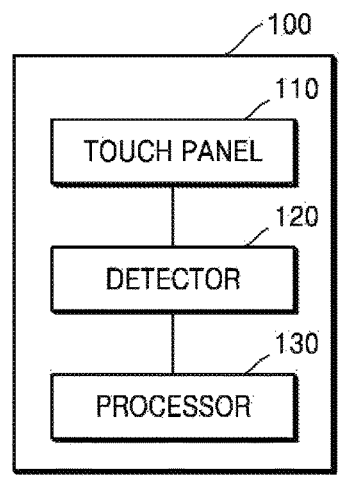
FIG. 1 is a block diagram showing a touch panel apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, the term "and/or" includes any and all combinations of one or more of the associated listed items. Expressions such as "at least one of," when preceding a list of elements, modify the entire list of elements and do not modify the individual elements of the list.

In this application, the terms "comprising" and "including" should not be construed to necessarily include all of the elements or steps disclosed herein, and should be construed not to include some of the elements or steps thereof, or should be construed to further include additional elements or steps.

Although the terms first, second, etc., may be used herein to describe various elements, these elements should not be limited by these terms. The above terms are used only to distinguish one component from another.

In this specification, the term "biosignal" collectively refers to a signal sensed in or induced by a human body and conceptually includes a bioelectric signal or bioimpedance signal. The bioelectric signal is a signal in the form of a current or voltage generated by a nerve cell or muscle cell. For example, an electrocardiogram, electromyogram, or electroencephalography signal corresponds to the bioelectric signal. The bioimpedance signal is a signal generated by a voltage drop that is caused by an impedance of a tissue when a certain current is applied to the tissue. The bioimpedance signal may provide important information regarding composition, a blood volume, and blood distribution of the tissue. For example, body fat may be measured using the bioimpedance signal.

The term "touch panel apparatus" used herein denotes an apparatus for sensing a signal when a user brings his/her body part in contact with a screen of the apparatus and collectively refers to all types of apparatus to which a touch panel, such as a touch screen, a touch pad, etc., is applied. The touch panel apparatus may be a mobile terminal such as a smart phone or a wearable device such as a smart glass or smart watch, but is not limited thereto. When a body part of a user is brought into contact with a text or image displayed on a display unit equipped with a touch panel, the touch panel apparatus may recognize an item selected by the user according to a contact point on the screen, process a command corresponding to the selected item, and display userdesired information on the screen. The touch panel apparatus may be implemented in various ways, such as a capacitive type, a resistive type, etc.

One or more exemplary embodiments relate to a touch panel apparatus for sensing a biosignal and a method of acquiring information about respiration of a user using the same.

FIG. 1 is a block diagram showing a touch panel apparatus 100 according to an exemplary embodiment. Accordingly, it is to be understood by those skilled in the art that other general-purpose elements may be further included in addition to the elements shown in FIG. 1.

The touch panel apparatus 100 may control manipulation of the touch panel apparatus 100 or sense a biosignal of a user based on a touch input signal of the user. To this end, the touch panel apparatus 100 may have two operation modes, that is, a manipulation mode and a measurement mode. The manipulation mode denotes a mode in which the screen of the touch panel apparatus 100 is manipulated based on the touch input signal. The measurement mode denotes a mode in which a biosignal is sensed and measured based on the touch input signal. The touch panel apparatus 100 may have at least two operation modes including the manipulation mode and the measurement mode.

The touch panel apparatus 100 may perform mode switching based on a mode switching request or touch input signal from a user. In addition, the touch panel apparatus 100 may recognize a hovering signal to operate in the manipulation mode or measurement mode. Accordingly, the touch input signal may be generated when the user comes into direct contact with the touch panel, and also when a hovering signal is generated by a user moving his/her body part over the touch panel.

In the manipulation mode, the touch panel apparatus 100 may process and display a screen based on a touch input signal input to the screen by the user. For example, when the user touches the screen of the touch panel apparatus 100 with two fingers to perform a pinch gesture (e.g., pinch-in gesture and pinch-out gesture), the touch panel apparatus 100 may sense a touch input signal corresponding to the pinch gesture of the user to increase or decrease the size of the screen and then display the screen. When the user places two fingers close together on the screen and moves them apart without lifting them from the screen, the touch panel apparatus 100 may recognize that a pinch-in gesture is input and zoom in to an image displayed on the screen. On the other hand, when the user places two fingers apart from each other on the screen and moves them toward each other without lifting them from the screen, the touch panel apparatus 100 may recognize that a pinch-out gesture is input and zoom out of an mage displayed on the screen. In an another example, when the user performs a pinch gesture on the screen of the touch panel apparatus 100 with his/her two fingers, the touch panel apparatus 100 may sense a hovering signal corresponding to the pinch gesture of the user to increase or decrease the size of the screen and then display the screen.

In the measurement mode, the touch panel apparatus 100 may sense and measure a biosignal based on a touch input signal input to the screen by the user. For example, when the user has not moved a body part for a certain time while the body part is in contact with the screen of the touch panel apparatus 100, the touch panel apparatus 100 may sense the biosignal based on a change in an electric field caused by the body part that is in contact with the screen.

Referring to FIG. 1, the touch panel apparatus 100 includes a touch panel 110, a detector 120, and a processor 130.

When the touch panel apparatus 100 operates in the measurement mode, the touch panel 110 may sense a biosignal based on the touch input signal of the user. For example, when the touch panel 110 is brought into contact with a first body part of the user, the touch panel apparatus 100 may operate in the measurement mode and thus the touch panel 110 may sense the biosignal from the first body part of the user. In this case, the first body part of the user may be a chest. A biosignal sensed from the chest of the user may be based on changes in capacitance that may correspond to changes in volume of the thoracic cavity of the user according to respiration. Such a biosignal may be sensed even when the touch panel 110 is not in direct contact with the chest.

In the touch panel apparatus 100, the detector 120 may detect a respiratory signal from the sensed biosignal. The detector 120 may filter a signal in a frequency band corresponding to the respiratory signal out of the sensed biosignal, remove noise from the filtered signal, and output a result of the removal as the respiratory signal.

In the touch panel apparatus 100, the processor 130 may acquire information about respiration of the user based on characteristics of the detected respiratory signal. The processor 130 may detect a maximum peak upon the inhalation of the user and a minimum peak upon the exhalation of the user from the respiratory signal detected by the detector 120 and may recognize characteristics of the respiratory signal in each respiratory cycle, which is a combination of the inhalation and the exhalation. The processor 130 may acquire the information about respiration of the user based on characteristics of the respiratory signal.

When the operation mode of the touch panel apparatus 100 is switched to the manipulation mode, the touch panel 110 may display the information about the respiration of the user. The processor 130 may acquire the information about the respiration of the user based on characteristics of the respiratory signal detected by the detector 120.

The touch panel apparatus 100 may transmit at least one of the biosignal, the respiratory signal, and the respiration information to a user terminal that interoperates with the touch panel apparatus 100. For example, the touch panel apparatus 100 may transmit at least one of the biosignal sensed by the touch panel 110, the respiratory signal detected by the detector 120, and the user respiration information acquired by the processor 130 to the user terminal. Thus, while using the touch panel apparatus 100 to sense the biosignal, detect the respiratory signal, or acquire the user respiration information, the user may check the sensed biosignal, the detected respiratory signal, or the acquired user respiration information through the user terminal that interoperates with the touch panel apparatus 100. After using the touch panel apparatus 100 to sense the biosignal or detect the respiratory signal, the user may transmit the sensed biosignal, the detected respiratory signal, or the acquired user respiration information to the user terminal that interoperates with the touch panel apparatus 100. The user terminal may include various kinds of devices, such as a mobile device, a wearable device, stationary device, etc.

Figure 2:
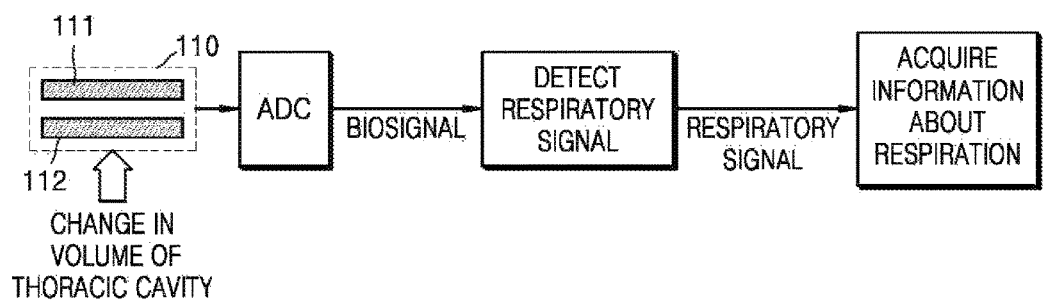
FIG. 2 is a view illustrating an operation of a touch panel apparatus according to an exemplary embodiment.

FIG. 2 is a view illustrating an operation of a touch panel apparatus according to an exemplary embodiment.

The touch panel 110 of the touch panel apparatus 100 may include a pair of electrode layers 111 and 112 that sense the touch input signal of the user. The touch panel apparatus 100 may sense the biosignal based on capacitance in the electrode layer pair 111 and 112 which changes according to the respiration of the user. The capacitance caused by the change in the volume of the thoracic cavity due to the respiration of the user may be induced to the electrode layer pair 111 and 112 included in the touch panel 110. This will be described in detail below with reference to FIG. 3.

The biosignal output from the touch panel 110 of the touch panel apparatus 100 may be converted into a digital signal through an analog-to-digital converter (ADC).

The detector 120 of the touch panel apparatus 100 may detect the respiratory signal from the biosignal. Since any signals or noise other than the respiratory signal may be included in the biosignal input to the detector 120, the detector 120 may extract the respiratory signal from the input biosignal. This will be described in detail below with reference to FIGS. 4 and 5.

The processor 130 of the touch panel apparatus 100 may acquire the user respiration information based on characteristics of the detected respiratory signal. This will be described in detail below with reference to FIGS. 6 to 9.

Figure 3:
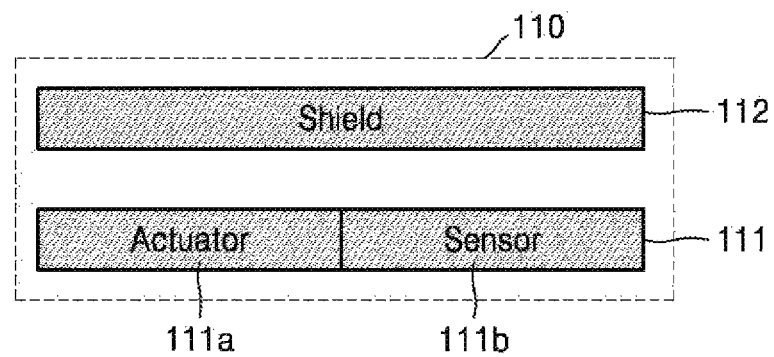
FIG. 3 is a view illustrating a touch panel included in a touch panel apparatus according to an exemplary embodiment.

FIG. 3 is a view illustrating a touch panel included in a touch panel apparatus according to an exemplary embodiment. Accordingly, it is to be understood by those skilled in the art that other general-purpose elements may be further included in addition to the elements shown in FIG. 3.

The touch panel 110 may sense the biosignal based on capacitance in the electrode layer pair which changes according to the respiration of the user. The touch panel 110 may include at least one pair of electrode layers 111 and 112, and one electrode layer pair may include a first electrode layer 111 and a second electrode layer 112. Each electrode layer 111 and 112 may be a transparent electrode layer, for example, an indium-tin-oxide (ITO) electrode layer. An insulator layer may be included between the first electrode layer 111 and the second electrode layer 112. The capacitance in the electrode layer pair 111 and 112 may vary depending on the type or form of the insulator layer.

When certain driving power is continuously applied while the touch panel apparatus 100 operates in the manipulation mode, the first electrode layer 111 may be maintained to be field-coupled with the second electrode layer 112. When the touch input signal is applied to the first electrode layer 111, the position or type of the touch input signal may be checked based on the change in the field-coupling. When the touch panel apparatus 100 is in the measurement mode, the second electrode layer 112 may be connected to the ground. When the second electrode layer 112 is grounded, the second electrode layer 112 may operate as a shield against the first electrode layer 111. In other words, when the second electrode layer 112 is connected to the ground, the second electrode layer 112 may operate as a shield that blocks a variety of noise from being transferred toward the first electrode layer 111. Thus, the first electrode layer 111 may sense a very small touch input signal from the outside without using the change in field coupling due to the driving power.

When the touch panel apparatus 100 is in the measurement mode, the first electrode layer 111 may be partitioned into regions with various shapes. For example, the first electrode layer 111 may be partitioned into at least two regions and also may be partitioned into regions with different sizes. As shown in FIG. 3, the first electrode layer 111 is partitioned into two regions, which may operate as an actuator 111a and a sensor 111b, respectively. The second electrode layer 112 may operate as a shield that blocks noise from entering the first electrode layer.

Figure 4:
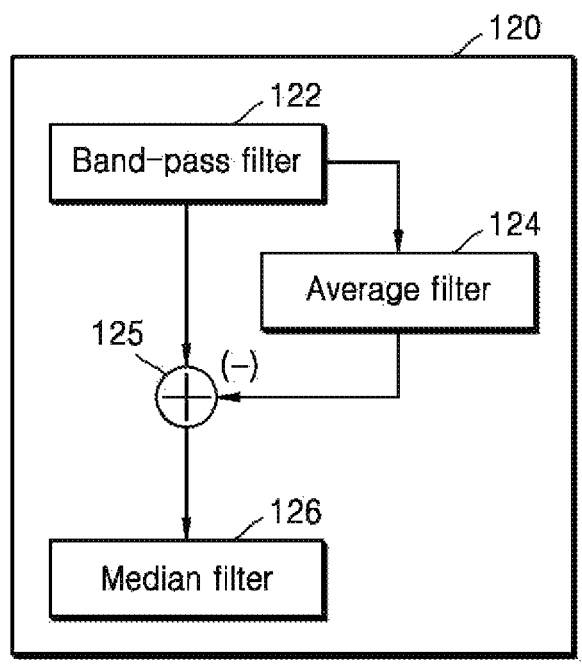
FIG. 4 is a view illustrating a detector included in a touch panel apparatus according to an exemplary embodiment.

FIG. 4 is a view illustrating a detector included in a touch panel apparatus according to an exemplary embodiment. Accordingly, it is to be understood by those skilled in the art that other general-purpose elements may be further included in addition to the elements shown in FIG. 4.

The detector 120 of the touch panel apparatus 100 may detect a respiratory signal from a biosignal. Since any signals or noise other than the respiratory signal may be included in the biosignal input to the detector 120, the detector 120 may have sub-elements that extract the respiratory signal from the input biosignal.

The detector 120 may include at least one filter configured to pass a signal in a frequency band corresponding to the respiratory signal (hereinafter referred to as a respiratory frequency band) among the biosignal and at least one noise removal filter configured to remove noise from the signal in the respiratory frequency band.

Referring to FIG. 4, the detector 120 of the touch panel apparatus 100 may include a band-pass filter 122, an average filter 124, an adder-subtractor 125, and a median filter 126. The band-pass filter 122 may receive a biosignal input to the detector 120, pass a signal in the respiratory frequency band (e.g., 0.2-0.8 Hz), and filter out a signal which is out of the respiratory frequency band. The average filter 124 may output an average signal of the signal in the respiratory frequency band that has passed through the band-pass filter 122. The adder-subtractor 120 may receive the bandpass signal from the band-pass filter 122 and the average signal from the average filter 124, subtract the average signal from the bandpass signal, and output the subtracted signal. The median filter 126 may receive the subtracted signal and may output a signal from which noise is removed therefrom as the respiratory signal. The average filter 124 and the adder-subtractor 125 may be omitted, and the median filter 126 may receive the bandpass signal directly from the band-pass filter 122.

Figure 5A:
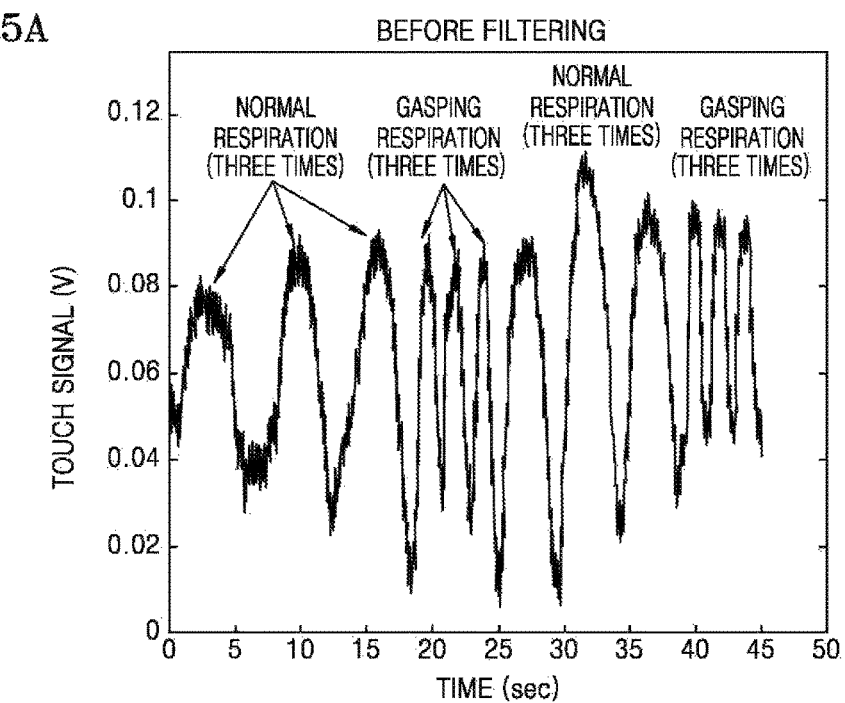
FIGS. 5A and 5B show graphs of respiratory signals before and after filtering according to an operation of a detector included in a touch panel apparatus according to an exemplary embodiment.
Figure 5B:
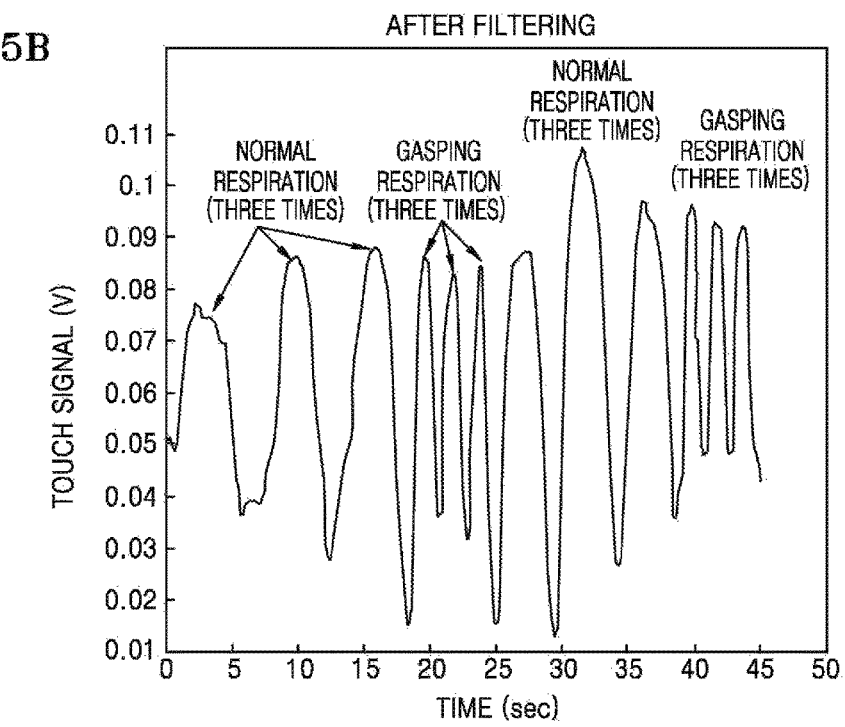

FIG. 5A and FIG. 5B show graphs of respiratory signals before and after filtering according to an operation of a detector included in a touch panel apparatus according to an exemplary embodiment.

Referring to FIG. 5A and FIG. 5B, graphs before and after filtering is performed to remove noise from a respiratory signal at a time in which a user alternately performs normal respiration and gasping respiration three times are shown. The graphs before and after the signal in the frequency band corresponding to the respiratory signal is extracted from the biosignal input to the detector 120 of the touch panel apparatus 100, and the filtering is performed on the extracted signal to remove the noise therefrom are shown.

An approximate form of the respiratory signal of the user may be checked from the graph before the filtering. However, it may be checked that noise is also included in addition to the respiratory signal.

The respiratory signal of the user after the noise is removed therefrom may be checked from the graph after the filtering. Compared with the graph before the filtering, peaks of respiratory signals upon the general respiration and the gasping respiration may be accurately checked.

Figure 6:
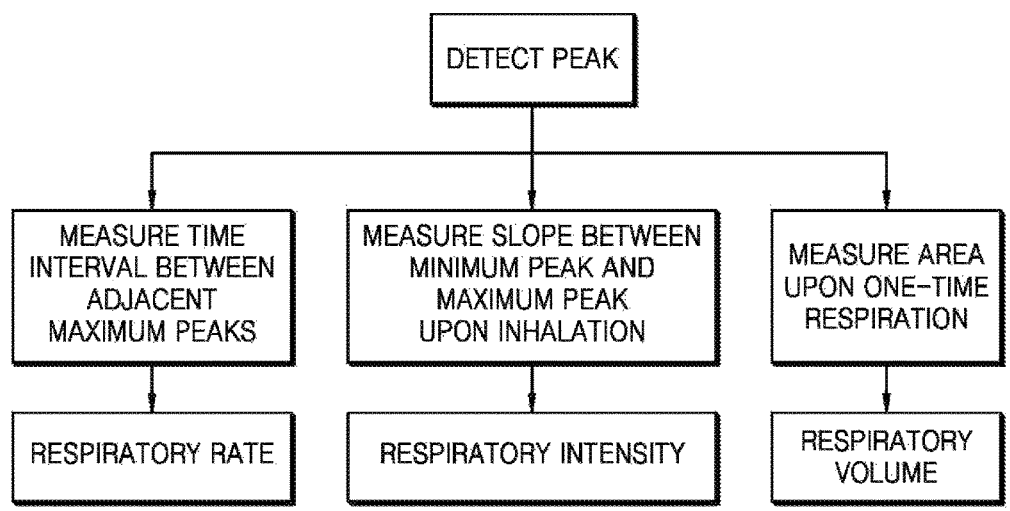
FIG. 6 is a view illustrating an operation of a processor included in a touch panel apparatus according to an exemplary embodiment.
Figure 7A:
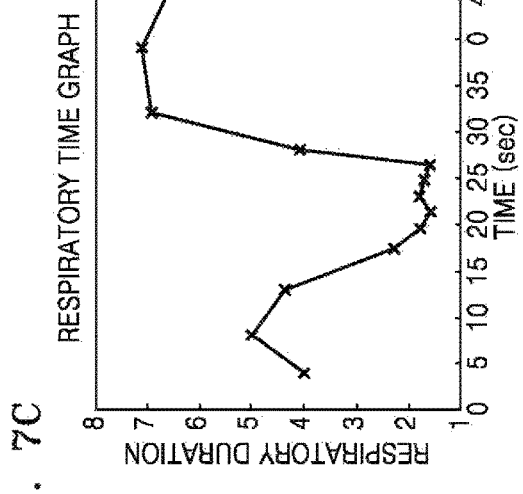
FIGS. 7A to 7D are views showing a process of acquiring information about a respiratory rate of a user by a processor included in a touch panel apparatus according to an exemplary embodiment.
Figure 7C:
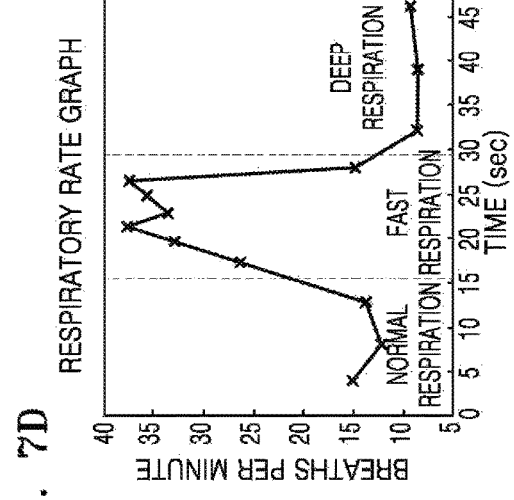
Figure 7B:
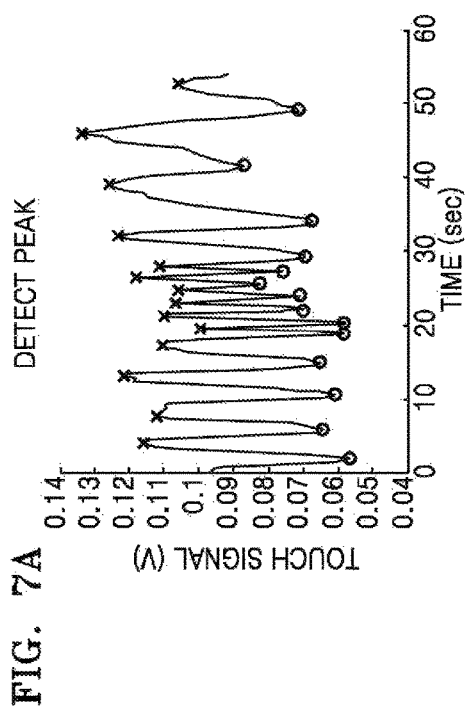
Figure 7D:
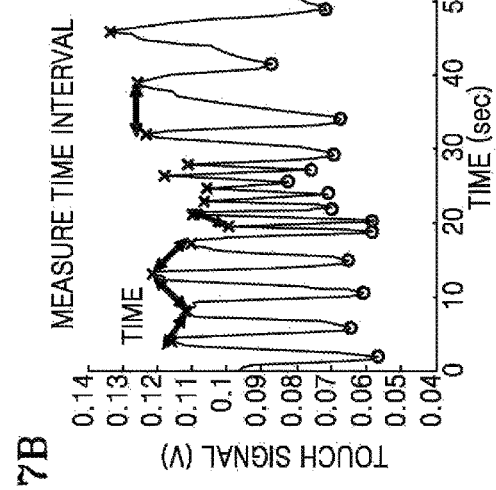

FIG. 6 is a view illustrating an operation of a processor included in a touch panel apparatus according to an exemplary embodiment.

The processor 130 of the touch panel apparatus 100 may acquire information about respiration of a user based on characteristics of the respiratory signal detected by the detector 120. The processor 130 may detect peaks from the respiratory signal to recognize characteristics of the respiratory signal. The processor 130 may use the detected peaks to acquire a variety of information about respiration of the user.

The processor 130 may detect peaks of the respiratory signal, measure a time interval between adjacent peaks, and acquire information about a respiratory rate of a user based on a result of the measurement. The processor 130 may measure a time interval between maximum peaks adjacent to each other from the respiratory signal and may acquire the information about the respiratory rate based on the measured time interval. Alternatively, the processor 130 may detect the number of maximum peaks for a certain time period (e.g., 60 seconds) while the user is at rest. The processor 130 may determine whether the measured respiratory rate is within a normal range based on average resting respiratory rates by age. For example, the touch panel apparatus 100 may store an average respiratory rate for a healthy adult as 12-18-breaths per minute and store the user's age. If the processor detects 15 maximum peaks for 60 seconds (i.e., 15-breaths per minute) and recognizes the user as an adult, the processor 120 may determine that the user's respiratory rate is normal based on the stored average respiratory rate for a healthy adult. This will be described in detail below with reference to FIGS. 7A to 7D.

The processor 130 may detect peaks of the respiratory signal, measure a slope between a minimum peak and a maximum peak upon the inhalation for each respiratory cycle, and acquire the information about respiratory intensity of the user based on a result of the measurement. The processor 130 may measure the slope between the minimum peak and the maximum peak upon the inhalation from the respiratory signal and may acquire the information about the respiratory intensity based on the measured slope. This will be described in detail below with reference to FIGS. 8A to 8C.

The processor 130 may detect peaks of the respiratory signal, measure an area of sections corresponding to the inhalation and the exhalation of each respiratory cycle, and acquire information about a respiratory volume of a user based on a result of the measurement. The processor 130 may measure an area of one-time respiration including an inhalation and an exhalation from the respiratory signal and acquire the information about the respiratory volume based on the measured area. This will be described in detail below with reference to FIGS. 9A to 9C.

The processor 130 may compare respiratory signals measured for a certain period and acquire information based on a result of the comparison. For example, the processor 130 may compare respiratory signals before and after exercise of the user and may acquire information about an exercise load applied to the user during the exercise or information about a recovery speed at which respiration after the exercise returns to respiration before the exercise. As another example, the processor 130 may recognize a pattern for the respiratory signal of the user and may evaluate a current stress state or tension of the user from the respiratory signal of the user based on the pattern.

FIGS. 7A to 7D are views illustrating a process of acquiring information about a respiratory rate of a user by a processor included in a touch panel apparatus according to an exemplary embodiment.

The processor 130 of the touch panel apparatus 100 may detect peaks of the respiratory signal, measure a time interval between adjacent peaks, and acquire information about a respiratory rate of the user based on a result of the measurement.

The processor 130 may detect peaks upon the inhalation and exhalation from the respiratory signal output by the detector 120. In a one-time respiratory cycle including an inhalation and an exhalation, the maximum peak may be formed upon the inhalation, and the minimum peak may be formed upon the exhalation. Referring to a respiratory signal graph of FIGS. 7A to 7D, a maximum peak upon the inhalation of each respiratory cycle is represented as a mark 'x,' and a minimum peak upon the exhalation of each respiratory cycle is represented as a mark 'o.' The maximum peaks and the minimum peaks are alternated according to the inhalation and exhalation.

The processor 130 may measure a time interval between adjacent peaks from the respiratory signal. For example, the processor 130 may measure a time interval between maximum peaks upon the inhalation of each respiratory cycle or measure a time interval between minimum peaks upon the exhalation of each respiratory cycle. Referring to FIGS. 7A to 7D, arrows are used to represent adjacent peaks among the maximum peaks upon the inhalation of each respiratory cycle. The processor 130 may acquire information about a respiratory time by measuring time intervals between adjacent peaks for all respiratory signals.

It can be seen, from the respiratory time graph shown in FIGS. 7A to 7D, how much time it takes for each respiratory cycle including an inhalation and an exhalation. As shown in FIGS. 7A to 7D, it can be seen that it takes about 4 seconds for a first respiratory cycle, it takes about 5 seconds for a second respiratory cycle, and it takes about 4.5 seconds for a third respiratory cycle. It can be seen that it takes about 2.5 seconds for a fourth respiratory cycle, which is almost a half of the time, and it takes about 1.5 to 2 seconds for fifth to ninth respiratory cycles. It can be seen that it takes about 4 seconds for a tenth respiratory cycle, and it takes about 6.5 to 7 seconds for eleventh to thirteenth respiratory cycles.

The processor 130 may acquire information about a respiratory rate from the information about the respiratory time. Referring to the time taken for each respiratory cycle as checked in the above respiratory time graph, it may be checked whether the respiratory rate was high or low. Assuming that an average respiratory time taken for an ordinary person to perform an inhalation and an exhalation is about 4.5 seconds, it can be seen that respiration is fast when it takes less than 4.5 seconds and respiration is slow or deep when it takes more than 4.5 seconds. Referring to the respiratory time graph shown in FIGS. 7A to 7D, it can be seen that the user performs normal respiration up to about 15 seconds, fast respiration up to about 27 seconds, and deep respiration since then.

Figure 8A:
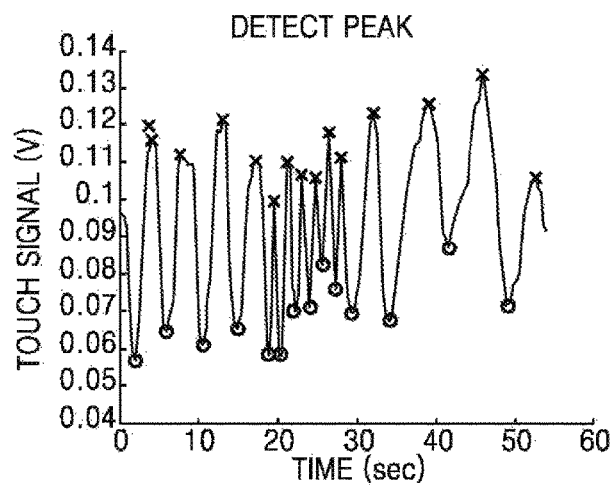
FIGS. 8A to 8C are views showing a process of acquiring information about respiratory intensity of a user by a processor included in a touch panel apparatus according to another exemplary embodiment.
Figure 8B:
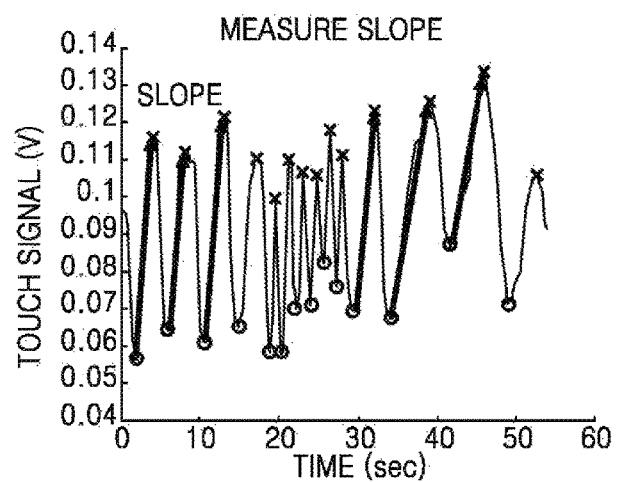
Figure 8C:
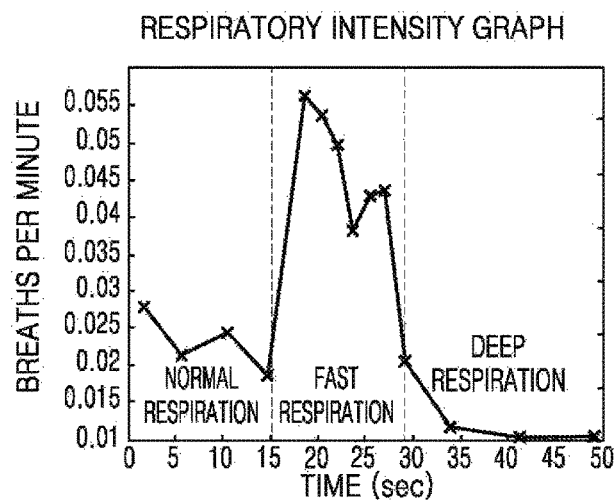

FIGS. 8A to 8C are views showing a process of acquiring information about respiratory intensity of a user by a processor included in a touch panel apparatus according to another exemplary embodiment.

The processor 130 may detect peaks of the respiratory signal, measure a slope between a minimum peak and a maximum peak upon the inhalation for each respiratory cycle, and acquire the information about respiratory intensity of the user based on a result of the measurement.

The processor 130 may detect peaks upon the inhalation and exhalation from the respiratory signal output by the detector 120. In a one-time respiratory cycle including an inhalation and an exhalation, the maximum peak may be formed upon the inhalation, and the minimum peak may be formed upon the exhalation. Referring to a respiratory signal graph of FIGS. 8A to 8C, a maximum peak upon the inhalation of each respiratory cycle is represented as a mark 'x,' and a minimum peak upon the exhalation of each respiratory cycle is represented as a mark 'o.' The maximum peak and the minimum peak are alternated according to the inhalation and exhalation.

The processor 130 may measure a slope between the minimum peak and the maximum peak upon the inhalation from the respiratory signal. Referring to FIGS. 8A to 8C, an arrow from the minimum peak to the maximum peak upon the inhalation is displayed. The processor 130 may acquire information about respiratory intensity by measuring a slope between the minimum peak and the maximum peak upon the inhalation with respect to all respiratory signals. The slope between the minimum peak and the maximum peak upon the inhalation is proportional to the respiratory intensity. In other words, the respiratory intensity increases as the slope increases and decreases as the slope decreases.

It can be seen, from the respiratory intensity graph shown in FIGS. 8A to 8C, how quickly the inhalation is performed for each respiratory cycle including the inhalation and the exhalation. Referring to FIGS. 8A to 8C, the slope between the minimum peak and the maximum peak upon the inhalation in the respiratory signal graph increases and then decreases, compared with the first several slopes. The respiratory intensity increases and then decreases since the first respiration.

Figure 9A:
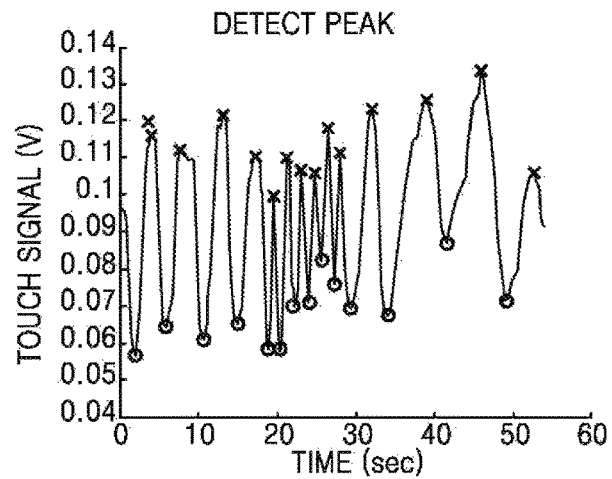
FIGS. 9A to 9C are views showing a process of acquiring information about a respiratory volume of a user by a processor included in a touch panel apparatus according to still another exemplary embodiment.
Figure 9B:
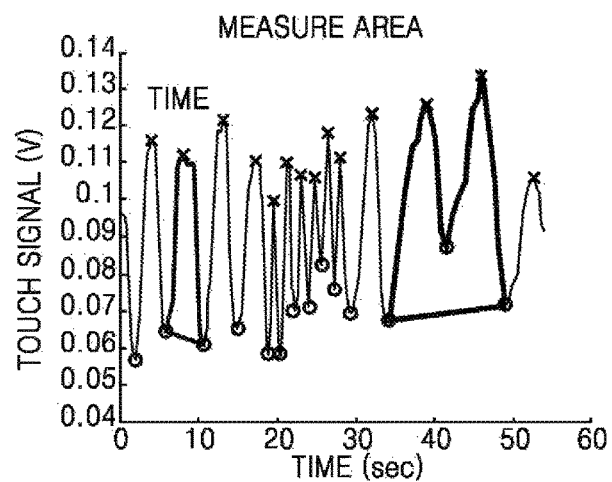
Figure 9C:
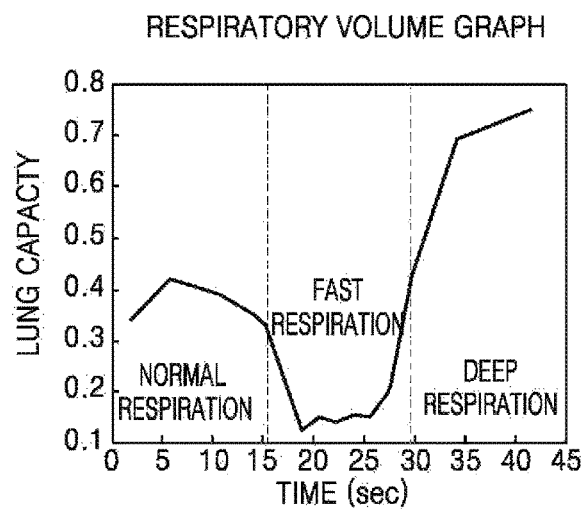

FIGS. 9A to 9C are views showing a process of acquiring information about a respiratory volume of a user by a processor included in a touch panel apparatus according to still another exemplary embodiment.

The processor 130 may detect peaks of the respiratory signal, measure an area of sections corresponding to an inhalation and an exhalation for each respiratory cycle, and acquire information about a respiratory volume of a user based on a result of the measurement.

The processor 130 may detect peaks upon the inhalation and exhalation from the respiratory signal output by the detector 120. In a one-time respiratory cycle including an inhalation and an exhalation, the maximum peak may be formed upon the inhalation, and the minimum peak may be formed upon the exhalation. Referring to a respiratory signal graph of FIGS. 9A to 9C, a maximum peak upon the inhalation of each respiratory cycle is represented as a mark 'x,' and a minimum peak upon the exhalation of each respiratory cycle is represented as a mark 'o.' The maximum peak and the minimum peak are alternated according to the inhalation and exhilaration.

The processor 130 may measure an area formed by sections corresponding to the inhalation and the exhalation for every respiratory cycle from the respiratory signal. Referring to FIGS. 9A to 9C, the processor 130 may acquire information about a respiratory volume by measuring a line from an inhalation start point to an inhalation start point of the next respiratory cycle and an area formed by respiratory signals in inhalation and exhalation sections. In this case, the area formed by the sections corresponding to the inhalation and exhalation is proportional to the respiratory volume. In other words, the respiratory volume increases as the area of the sections corresponding to the inhalation and exhalation increases and decreases as the area decreases.

The change in a respiratory volume for each respiratory cycle including an inhalation and an exhalation can be seen from the respiratory time graph shown in FIGS. 9A to 9C. Referring to FIGS. 9A to 9C, the area formed by the sections corresponding to the inhalation and exhalation for each respiratory cycle decreases and then increases, compared with first several areas. The respiratory volume decreases and then increases since the first respiration. The decrease in the respiratory volume denotes gasping respiration or fast respiration, and the increase in the respiratory volume denotes deep respiration.

Figure 10:
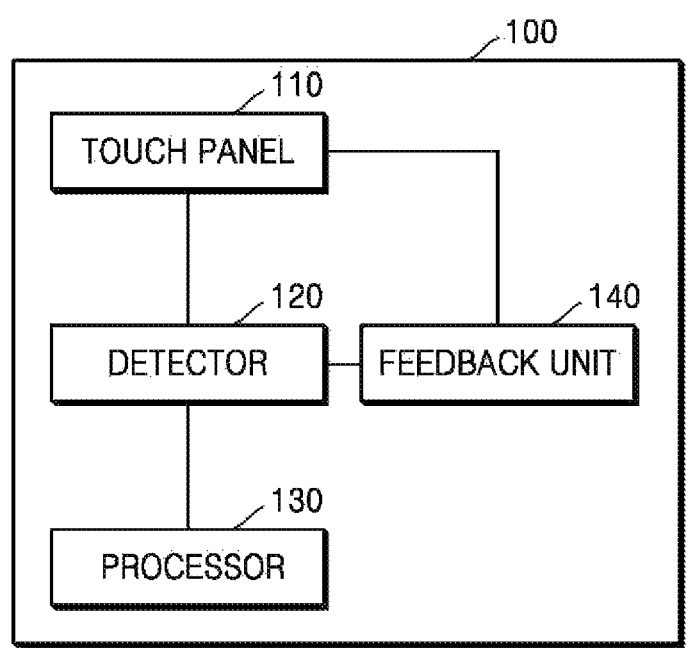
FIG. 10 is a block diagram showing a touch panel apparatus according to another embodiment.

FIG. 10 is a block diagram showing a touch panel apparatus according to another exemplary embodiment. Accordingly, it is to be understood by those skilled in the art that other general-purpose elements may be further included in addition to the elements shown in FIG. 10. What has been described above will not be described in detail below.

Referring to FIG. 10, the touch panel apparatus 100 includes a touch panel 110, a detector 120, a processor 130, and a feedback unit 140.

When the touch panel apparatus 100 operates in the measurement mode, the touch panel 110 may sense a biosignal based on a touch input signal of a user.

In the touch panel apparatus 100, the detector 120 may detect a respiratory signal from the sensed biosignal. The detector 120 may filter a signal in a frequency band corresponding to the respiratory signal out of the sensed biosignal, remove noise from the filtered signal, and output a result of the removal as the respiratory signal.

In the touch panel apparatus 100, the processor 130 may acquire information about respiration of the user based on characteristics of the detected respiratory signal.

The feedback unit 140 may inversely amplify a respiration-removed signal, which is a signal obtained by removing the respiratory signal from the biosignal, and may output the respiration-removed signal to the touch panel 110 that senses the biosignal. The feedback unit 140 may be implemented with an inverting amplifier. When the touch panel 110 senses the biosignal, the touch panel 110 may receive, as a negative feedback, a respiration-removed signal in a respiratory cycle corresponding to a certain period from the feedback unit 140. In this case, the respiratory cycle corresponding to the certain period may be a period corresponding to an immediately previous respiratory cycle or several previous respiratory cycles. An operation of the touch panel apparatus 100 will be described in more detail below with reference to FIG. 11.

Figure 11:
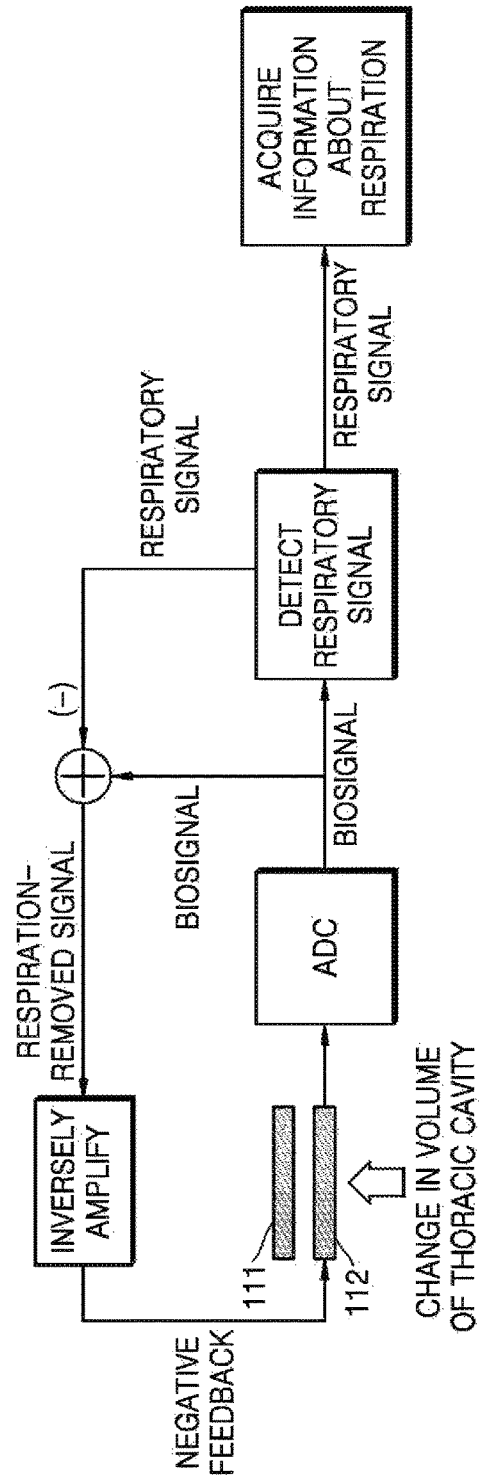
FIG. 11 is a view illustrating an operation of a touch panel apparatus according to another exemplary embodiment.

FIG. 11 is a view illustrating an operation of a touch panel apparatus according to another exemplary embodiment.

The touch panel 110 of the touch panel apparatus 100 may include a pair of electrode layers 111 and 112 that sense a touch input signal of a user. The touch panel apparatus 100 may sense the biosignal based on capacitance in the electrode layer pair 111 and 112 which changes according to the respiration of the user. The capacitance caused by the change in the volume of thoracic cavity due to the respiration of the user may be induced to the electrode layer pair included in the touch panel 110.

The biosignal output from the touch panel 110 of the touch panel apparatus 100 may be converted into a digital signal through an analog-to-digital converter (ADC).

The detector 120 of the touch panel apparatus 100 may detect the respiratory signal from the biosignal. Since signals or noise other than the respiratory signal may be included in the biosignal input to the detector 120, the detector 120 may extract the respiratory signal from the input biosignal.

The processor 130 of the touch panel apparatus 100 may acquire the user respiration information based on characteristics of the detected respiratory signal.

A signal such as the biosignal input to the detector 120 of the touch panel apparatus 100 and a signal such as the respiratory signal output by the detector 120 may be input to the feedback unit 140. The feedback unit 140 may generate a respiration-removed signal by removing the input respiratory signal from the input biosignal. In addition, the feedback unit 140 may inversely amplify the respiration-removed signal and then output the inversely amplified signal to the touch panel 110. In other words, the feedback unit 140 may input the inversely amplified respiration-removed signal to the touch panel 110 as a negative feedback. As the negative feedback is repeated, the respiration-removed signal gradually decreases, and the intensity of the respiratory signal increases. Thus, a signal-to-noise ratio may increase.

Figure 12:
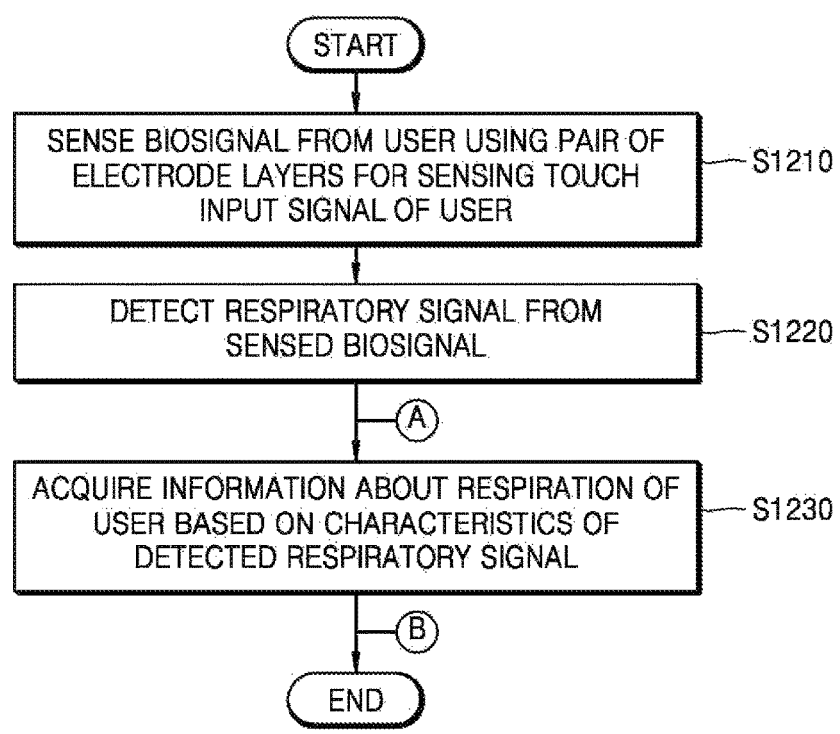
FIG. 12 is a flowchart illustrating a method of acquiring information about respiration of a user using a touch panel apparatus according to an exemplary embodiment.

FIG. 12 is a flowchart illustrating a method of acquiring information about respiration of a user using a touch panel apparatus according to an exemplary embodiment. A description of the above-described touch panel apparatus for sensing the biosignal will be omitted, but may be applied without change thereof.

In operation S1210, the touch panel apparatus 100 may sense a biosignal from a user using a pair of electrode layers 111 and 112 that senses a touch input signal of the user. The touch panel apparatus 100 may sense the biosignal based on capacitance in the electrode layer pair 111 and 112 which changes according to the respiration of the user. In this case, the electrode layer pair 111 and 112 may include a first electrode layer 111 partitioned into a plurality of regions and configured to operate as an actuator and a sensor and a second electrode layer 112 configured to operate as a shield that blocks noise from entering the first electrode layer. The touch panel apparatus 100 may sense the biosignal using the first electrode layer 111 and the second electrode layer 112.

The touch panel apparatus 100 may receive a respiration-removed signal, which is a signal obtained by removing the respiratory signal from the biosignal in a respiratory cycle corresponding to a certain period, as a negative feedback and may sense the biosignal.

In operation S1220, the touch panel apparatus 100 may detect a respiratory signal from the sensed biosignal. For example, the touch panel apparatus 100 may pass a signal in a frequency band corresponding to the respiratory signal (hereinafter, a respiratory frequency band) among the sensed biosignal, filter out a signal that is out of the respiratory frequency band. The touch panel apparatus 100 may remove noise from the passed signal, and detect the respiratory signal.

In operation S1230, the touch panel apparatus 100 may acquire information about respiration of the user based on characteristics of the detected respiratory signal. In order to recognize the characteristics of the detected respiratory signal, the touch panel apparatus 100 may detect peaks from the respiratory signal and acquire a variety of information about the respiration of the user.

The touch panel apparatus 100 may acquire information about the user's respiration based on a currently measured respiratory signal. Further, the touch panel apparatus 100 may compare respiratory signals measured during a certain period with each other and acquire information based on a result of the comparison. For example, the touch panel apparatus 100 may compare respiratory signals before and after exercise of the user and may acquire information about an exercise load applied to the user during the exercise or information about a recovery speed at which respiration after the exercise returns to respiration before the exercise. As another example, the touch panel apparatus 100 may recognize a pattern for the respiratory signal of the user and may evaluate a current stress state or tension of the user from the respiratory signal of the user based on the pattern.

Figure 13:
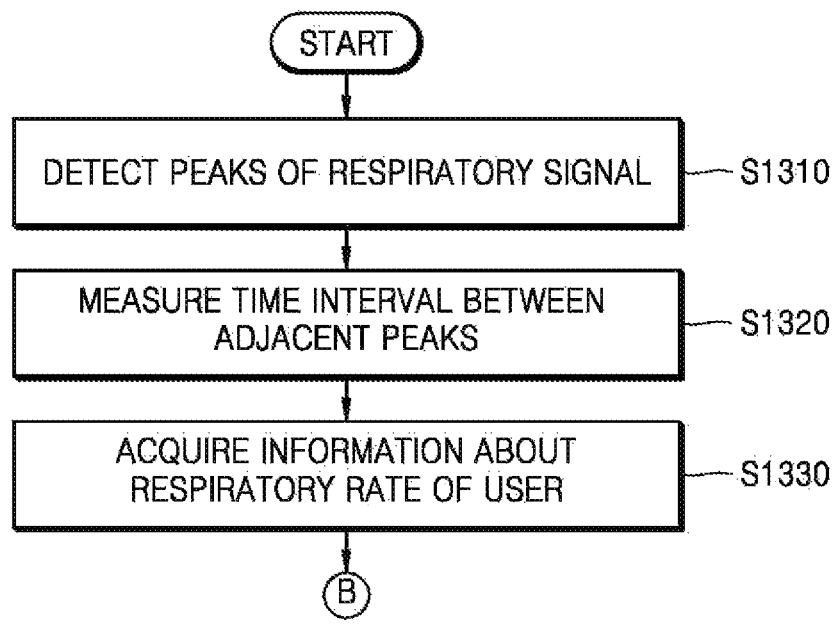
FIG. 13 is a detailed flowchart showing an operation of acquiring information about respiration of a user in a method of acquiring information about respiration of a user using a touch panel apparatus according to an exemplary embodiment.

FIG. 13 is a detailed flowchart showing an operation of acquiring information about respiration of a user using a touch panel apparatus according to an exemplary embodiment. FIG. 13 shows that the touch panel apparatus 100 acquires information about a respiratory rate of the user based on the respiratory signal.

In operation S1310, the touch panel apparatus 100 may detect peaks of a respiratory signal. The touch panel apparatus 100 may detect peaks upon an inhalation and an exhalation from the respiratory signal.

In operation S1320, the touch panel apparatus 100 may measure a time interval between adjacent peaks. The touch panel apparatus 100 may measure a time interval between maximum peaks upon the inhalation for each respiratory cycle or measure a time interval between minimum peaks upon exhalation for each respiratory cycle.

In operation S1330, the touch panel apparatus 100 may acquire information about a respiratory rate of a user based on a result of the measurement. Referring to a time taken for each respiratory cycle, the touch panel apparatus 100 may check whether the respiratory rate is high or low.

Figure 14:
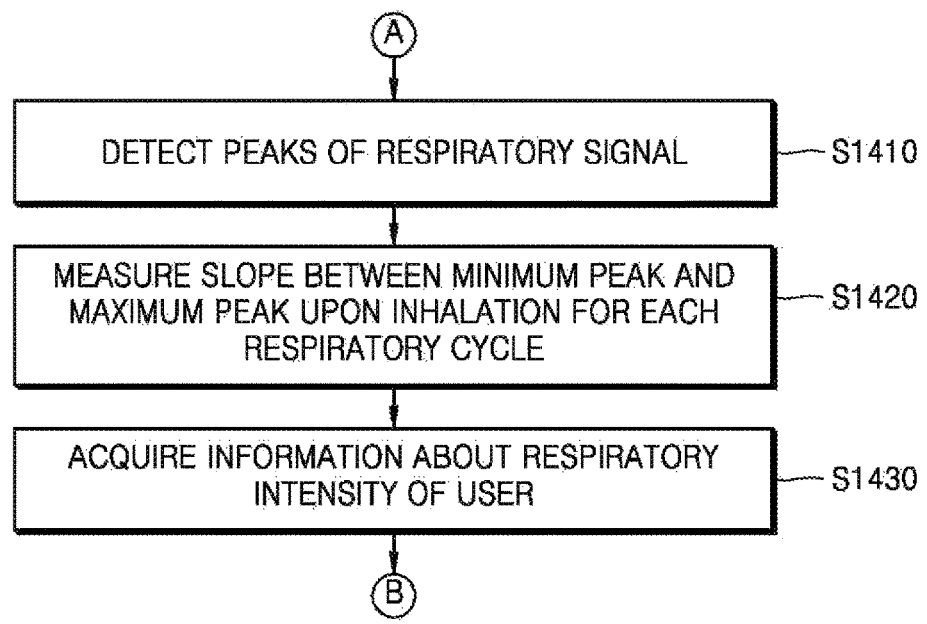
FIG. 14 is a detailed flowchart showing an operation of acquiring information about respiration of a user in a method of acquiring information about respiration of a user using a touch panel apparatus according to another exemplary embodiment.

FIG. 14 is a detailed flowchart showing an operation of acquiring information using a touch panel apparatus according to another exemplary embodiment. FIG. 14 shows that the touch panel apparatus 100 acquires information about respiratory intensity of the user based on the respiratory signal.

In operation S1410, the touch panel apparatus 100 may detect peaks of a respiratory signal. The touch panel apparatus 100 may detect peaks upon an inhalation and an exhalation from the respiratory signal.

In operation S1420, the touch panel apparatus 100 may measure a slope between a minimum peak and a maximum peak upon the inhalation for each respiratory cycle.

In operation S1430, the touch panel apparatus 100 may acquire information about respiratory intensity of a user based on a result of the measurement. The touch panel apparatus 100 may determine that the respiratory intensity increases as the slope between the minimum peak and the maximum peak upon the inhalation increases and may determine that the respiratory intensity decreases as the slope decreases.

Figure 15:
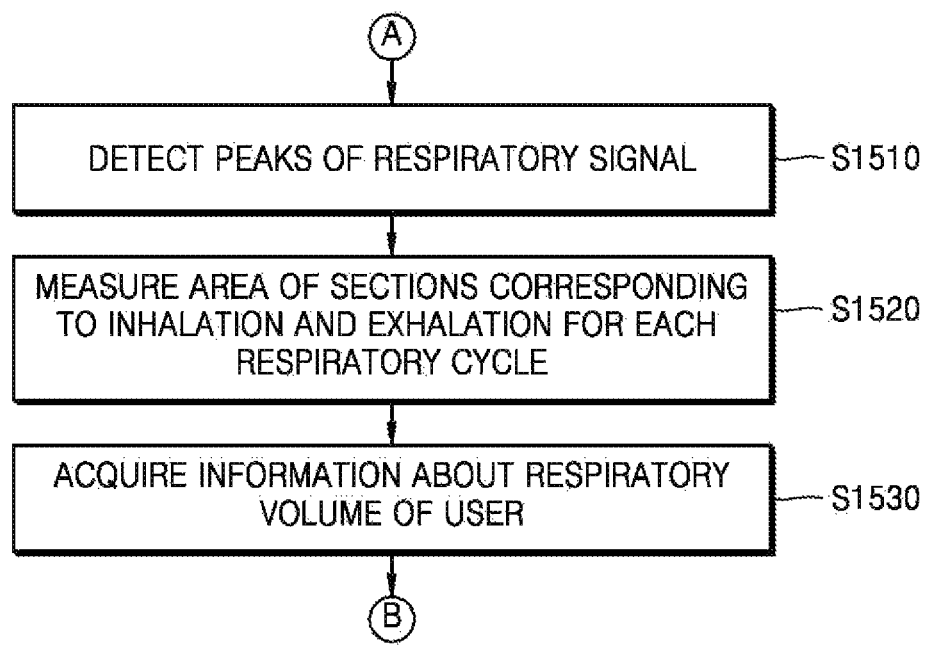
FIG. 15 is a detailed flowchart showing an operation of acquiring information about respiration of a user in a method of acquiring information about respiration of a user using a touch panel apparatus according to still another exemplary embodiment.

FIG. 15 is a detailed flowchart showing an operation of acquiring information about respiration of a user using a touch panel apparatus according to still another exemplary embodiment. FIG. 15 shows that the touch panel apparatus 100 acquires information about a respiratory volume of the user based on the respiratory signal.

In operation S1510, the touch panel apparatus 100 may detect peaks of a respiratory signal. The touch panel apparatus 100 may detect peaks upon an inhalation and an exhalation from the respiratory signal.

In operation S1520, the touch panel apparatus 100 may measure an area of sections corresponding to the inhalation and the exhalation for each respiratory cycle.

In operation S1530, the touch panel apparatus 100 may acquire information about a respiratory volume of a user based on a result of the measurement. The touch panel apparatus 100 may determine that the respiratory volume increases as the area of the sections corresponding to the inhalation and the exhalation increases and determine that the respiratory volume decreases as the area decreases.

The method of acquiring information about the respiration of the user using the above-described touch panel apparatus may be embodied as computer-readable code on a computer-readable recording medium. The computer-readable recording medium is any data storage device that can store data that can be thereafter read by a computer system. Examples of the computer-readable recording medium may include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A touch panel apparatus comprising:
   a touch panel configured to perform mode switching between a manipulation mode and a measurement mode based on a mode switching request,
   wherein in the measurement mode,
   the touch panel is configured to sense a capacitance sensing signal that indicates a change in capacitance of the touch panel when a user touches the touch panel;
   a detector configured to detect a respiratory signal from the sensed capacitance sensing signal; and
   a processor configured to acquire information about respiration of the user based on characteristics of the detected respiratory signal.

2. The touch panel apparatus of claim 1, wherein the touch panel comprises a pair of electrode layers and is further configured to sense the capacitance sensing signal that indicates the change in capacitance between the pair of electrode layers.

3. The touch panel apparatus of claim 1, wherein the touch panel comprises a pair of electrode layers,
   wherein the pair of electrode layers comprises a first electrode layer partitioned into a plurality of regions corresponding to an actuator and a sensor, a second electrode layer configured to block noise from entering the first electrode layer, and
   wherein the touch panel is further configured to sense the capacitance sensing signal that indicates the change in capacitance between the first electrode layer and the second electrode layer.

4. The touch panel apparatus of claim 1, wherein the detector comprises:
   a band pass filter configured to receive the capacitance sensing signal from the touch panel and pass a signal in a respiratory frequency band among the capacitance sensing signal; and
   at least one noise removal filter configured to remove noise from the signal in the respiratory frequency band, and supply to the processor the signal from which the noise is removed.

5. The touch panel apparatus of claim 1, wherein the processor is further configured to detect peaks of the respiratory signal, measure a time interval between adjacent peaks among the detected peaks, and determine a respiration rate of the user based on the measured time interval.

6. The touch panel apparatus of claim 1, wherein the processor is further configured to detect peaks of the respiratory signal, measure a slope between a minimum peak and a maximum peak upon an inhalation for each respiratory cycle among the detected peaks, and determine respiratory intensity of the user based on the measured slope.

7. The touch panel apparatus of claim 1, wherein the processor is further configured to detect peaks of the respiratory signal, measure an area of sections that corresponds to an inhalation and an exhalation for each respiratory cycle and is defined by at least three of the detected peaks, and determine a respiratory volume of the user based on the measured area.

8. The touch panel apparatus of claim 1, wherein the processor compares the capacitance sensing signal before exercise of the user and the capacitance sensing signal after the exercise of the user to determine an exercise load applied to the user during the exercise or a recovery speed at which a respiration rate after the exercise returns to a respiration rate before the exercise.

9. The touch panel apparatus of claim 1, wherein the touch panel apparatus further comprises a feedback unit configured to inversely amplify a respiration-removed signal that is obtained by removing the respiratory signal from the capacitance sensing signal, and output the inversely amplified respiration-removed signal,
   wherein the touch panel receives the respiration-removed signal as a negative feedback to adjust the capacitance sensing signal.

10. The touch panel apparatus of claim 1, wherein the touch panel apparatus is interoperable with a user terminal and configured to transmit information about the respiratory signal to the user terminal.

11. The touch panel apparatus of claim 1,
    wherein in the manipulation mode,
    the processor is further configured to manipulate a screen of the touch panel based on a touch input signal.

12. A method of acquiring information about respiration of a user by a touch panel apparatus, the method comprising:
    performing mode switching between a manipulation mode and a measurement mode based on a mode switching request;
    wherein in the manipulation mode, the method further comprises:
    sensing a capacitance sensing signal that indicates a change in capacitance of a touch panel when the user touches the touch panel apparatus;
    detecting a respiratory signal from the sensed capacitance sensing signal; and
    acquiring information about respiration of the user based on characteristics of the detected respiratory signal.

13. The method of claim 12, wherein the sensing the capacitance sensing signal comprises sensing the change in capacitance between a pair of electrode layers included in the touch panel apparatus.

14. The method of claim 12, wherein the sensing the capacitance sensing signal comprises sensing the change in capacitance between a first layer and a second layer included in the touch panel apparatus, and
    wherein the first electrode layer is partitioned into a plurality of regions and configured to operate as an actuator and a sensor, and the second electrode layer configured to operate as a shield that blocks noise from entering the first electrode layer.

15. The method of claim 12, further comprising:
receiving the capacitance sensing signal from the touch panel;
passing a signal in a respiratory frequency band among the capacitance sensing signal;
blocking a signal out of the respiratory frequency band among the capacitance sensing signal; and
removing noise from the signal in the respiratory frequency band.

16. The method of claim 15, wherein the signal in the respirator frequency band is a respirator sign, and
wherein the sensing the capacitance sensing signal comprises receiving a respiration-removed signal, which is obtained by removing the respiratory signal from the capacitance sensing signal, as a negative feedback to adjust the capacitance sensing signal.

17. The method of claim 12, further comprising:
measuring a time interval between two adjacent peaks of capacitance sensing signal; and
determining a respiratory rate of the user based on the measured time interval.

18. The method of claim 12, wherein the acquiring the information comprises:
detecting peaks of the respiratory signal;
measuring a slope between a minimum peak and a maximum peak upon an inhalation for each respiratory cycle among the detected peaks; and
generating respiratory intensity of the user based on the measured slope.

19. The method of claim 12, wherein the acquiring the information comprises:
detecting peaks of the respiratory signal;
measuring an area of sections that corresponds to an inhalation and an exhalation for each respiratory cycle and is defined by at least three of the detected peaks; and
determining a respiratory volume of the user based on the measured area.

20. The method of claim 12, further comprising comparing the capacitance sensing signal before exercise of the user and the capacitance sensing signal after exercise of the user to determine an exercise load applied to the user during the exercise or a recovery speed at which a respiration rate after the exercise returns to a respiration rate before the exercise.

21. A non-transitory computer readable storage medium storing a program that is executable by a computer to perform the method of claim 12.

22. The method of claim 12, wherein in the manipulation mode, the method further comprises:
manipulating a screen of the touch panel based on a touch input signal.

23. A touch panel apparatus comprising:
a touch panel configured to perform mode switching between a manipulation mode and a measurement mode based on a mode switching request,
wherein in the measurement mode,
the touch panel is configured to sense a capacitance sensing signal that indicates a change in capacitance of the touch panel when a user touches the touch panel;
a detector configured to detect a number of maximum peaks of the capacitance sensing signal within a predetermined time period; and
a processor configured to determine a respiration rate of the user based on the detected number of maximum peaks of the capacitance sensing signal within the predetermined time period.

24. The touch panel apparatus of claim 23, wherein the touch panel apparatus is configured to store information of an age of the user, and
wherein the processor is further configured to determine a health state of the user based on the determined respiration rate and the information of the age.

* * * * *